United States Patent
Vincent et al.

(10) Patent No.: US 10,877,033 B2
(45) Date of Patent: Dec. 29, 2020

(54) METHOD OF DETECTING THE PRESENCE OR ABSENCE OF AUTOANTIBODIES

(71) Applicant: Isis Innovation Limited, Oxford (GB)

(72) Inventors: Angela Vincent, Oxford (GB); Patrick Joseph Waters, Oxford (GB); Alexandru Radu Aricescu, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 286 days.

(21) Appl. No.: 14/899,523

(22) PCT Filed: Jun. 18, 2014

(86) PCT No.: PCT/GB2014/051874
§ 371 (c)(1),
(2) Date: Dec. 17, 2015

(87) PCT Pub. No.: WO2014/202978
PCT Pub. Date: Dec. 24, 2014

(65) Prior Publication Data
US 2016/0139119 A1 May 19, 2016

(30) Foreign Application Priority Data

Jun. 18, 2013 (GB) .................... 1310855.0
Jul. 25, 2013 (GB) .................... 1313249.3

(51) Int. Cl.
*G01N 33/564* (2006.01)
*G01N 33/574* (2006.01)

(52) U.S. Cl.
CPC ..... *G01N 33/564* (2013.01); *G01N 33/57488* (2013.01); *G01N 2800/285* (2013.01); *G01N 2800/50* (2013.01)

(58) Field of Classification Search
None
See application file for complete search history.

(56) References Cited

U.S. PATENT DOCUMENTS

2003/0148454 A1  8/2003  Marshak-Rothstein et al.

FOREIGN PATENT DOCUMENTS

| DE | 3721790 A1 | 1/1989 |
|---|---|---|
| WO | 199800164 A1 | 1/1998 |
| WO | 2002062378 A2 | 8/2002 |
| WO | 2003016522 A2 | 2/2003 |
| WO | 2008092164 A2 | 7/2008 |
| WO | 2011058052 A1 | 5/2011 |
| WO | 2012104837 A1 | 8/2012 |

OTHER PUBLICATIONS

Gronwell, C. and Silverman, G.J. J. Clin. Immunol. 2014;34(Suppl 1):S12-S21.*
Vincent, T., et al. J. Immunol. 2008;181:5730-5737 (Year: 2008).*
Nilsson et al., "Autoantibodies to Prostasomes as New Markers for Prostate Cancer", Upsala J Medical Science, (2001) 106:43-50.
Brouwer et al., "Autoantibodies directed to novel components of the PM/Scl complex, the human exosome", Arthritis Research, (2001) 4(2):134-138.
El Andaloussi et al., "Exosome-mediated delivery of siRNA in vitro and in vivo", Nature Protocols, (2012) 7:2112-2126.
Leite et al. "IgG1 antibodies to acetylcholine receptors in 'seronegative' myasthenia gravis", Brain, (2008) 131:1940-1952.
Dalmau et al., Paraneoplastic syndromes of the CNS, Lancet Neurology, (2008) 7(4):327-340.
Lai et al., "Investigation of LGI1 as the antigen in limbic encephalitis previously attributed to potassium channels: a case series", Lancet Neurology, (2010) 9:776-785.
Irani et al., "Antibodies to Kv1 potassium channel-complex proteins leucine-rich, glioma inactivated 1 protein and contactin-associated protein-2 in limbic encephalitis, Morvan's syndrome and acquired neuromyotonia", Brain, (2010) 133:2734-2748.
Littleton et al., "Immunocapture and Identification of Cell Membrane Protein Antigenic Targets of Serum Autoantibodies", Mol Cell Proteomics, (2009) 8: 1688-96.
Henry et al., "Improved methods for producing outer membrane vesicles in Gram-negative bacteria", Research in Microbiology, (2004) 155:437-446.
Estelles et al., "Exosome nanovesicles displaying G protein-coupled receptors for drug discovery", International Journal of Nanomedicine, (2007) 2(4):751-760.
Faini et al., "Vesicle coats: structure, function, and general principles of assembly", Trends in Cell Biology, (2013) 23(6):279-288.
El Andaloussi et al., "Extracellular vesicles: biology and emerging therapeutic opportunities", Nature Reviews Drug Discovery, (2013) 12:347-357.
Vikram B. Kasaragod, et al.; Structure-Function Relationships of Glycine and GABA A Receptors and Their Interplay with Scaffolding Protein Gephyrin, Frontiers in Molecular Neuroscience, Published online Sep. 12, 2018.
Iorio, Raffaele, et al; "Astrocytic Autoantibody of Neuromyelitis Optica (NMO-IgG) Binds to Aquaporin-4 Extracellular Loops, Monimers, Tetramers and High Order Arrays"; National Institutes of Health, J. Autoimmun Feb. 2013; 40: 21-27.
Carrasquillo, Karen G., et al; "Relationship Between Conformational Stability and Lyophilization-induced Structural Changes in Chymotrypsin"; Biotechnol. Appl. Biochem. (2000) 31, 41-53.

* cited by examiner

*Primary Examiner* — G. R. Ewoldt
(74) *Attorney, Agent, or Firm* — Norton Rose Fulbright US LLP

(57) ABSTRACT

The invention relates to methods of detecting the presence or absence of autoantibodies in an individual and to related methods and kits. In particular, the disclosure concerns measuring from one or more samples from an individual suspected of having a disease with an autoimmune component for binding of one or more autoantibodies to membrane vesicles comprising corresponding one or more antigens.

9 Claims, 6 Drawing Sheets

METHOD OF DETECTING THE PRESENCE OR ABSENCE OF AUTOANTIBODIES

CROSS REFERENCE TO RELATED APPLICATIONS

This application is a national phase application under 35 U.S.C. § 371 that claims priority to International Application No. PCT/GB2014/051874 filed Jun. 18, 2014, which claims priority to Great Britain Patent Application No. 1313249.3 filed Jul. 25, 2013 and Great Britain Patent Application No. 1310855.0 filed Jun. 18, 2013 all of which are incorporated herein by reference in their entirety.

FIELD OF THE INVENTION

The invention relates to methods of detecting the presence or absence of autoantibodies in an individual and to related methods and kits.

BACKGROUND OF THE INVENTION

There is increasing clinical relevance in autoantibodies that bind to the surface of muscle fibres at the nerve muscle junction, or to neurons (grey matter) or glial cells (white matter) in the nervous system. These autoantibodies are associated with specific diseases or conditions. Examples are myasthenia gravis which leads to muscle weakness and excessive fatigue, limbic encephalitis that involves severe memory loss, seizures and personality change or psychosis, and neuromyelitis optica that causes blindness and paralysis of the limbs with sensory disturbance and pain. The recognition of these conditions is important because the autoantibodies are thought to be disease causing and the duration of illness and outcomes can be substantially improved by treatments that reduce the autoantibodies such as plasma exchange, corticosteroids, immunosuppressives or therapeutic antibodies. It is also beginning to be appreciated that autoantibodies may be responsible for a proportion of patients with more common diseases such as some forms of epilepsy, dementia or psychosis. All of these diseases can occur in patients of any age, gender and sometimes in the context of a cancer. They are often acute and severe with long-stays in hospital if not treated effectively.

The commercial assays available to date to detect autoantibodies rely on labelling of the antigen in crude tissue or cell line extracts using radiolabelled neurotoxins that bind specifically to the antigen (e.g. radioimmunoprecipitations for acetylcholine receptor (AChR), voltage-gated calcium channel (VGCC), voltage-gated potassium channel (VGKC)-complex proteins) or purification of the proteins from recombinant sources (e.g. AChR, glutamic acid decarboxylase (GAD), muscle specific tyrosine kinase (MuSK)) for ELISA assays, or more recently use of "cell-based" assays. In the cell based assays, the antigen of interest is expressed by transfection with the appropriate DNA, or using viral vectors, usually in human embryonic kidney (HEK) cells. Stably transfected or transformed cells can also be used. In the commercial setting, the cells are fixed either in formaldehyde or acetone to enable storage and transport. The serum or cerebrospinal fluid (CSF) of the individual is applied to these cells, and binding of the antibodies to the antigen is detected with a second immunofluorescent antibody. However, fixing the cells reduces the sensitivity of the assay to different degrees, depending on the antigen involved, increases the background and enables the detection of antibodies that are not likely to be relevant since the cytosol of the cells is not neuronal.

SUMMARY OF THE INVENTION

The inventors have shown that a preparation of membranes or membrane derived vesicles (herein defined as membrane vesicles) comprising an antigen on their surface can be used in a method of detecting the presence or absence of an autoantibody directed against the antigen in an individual. The preparation of membrane vesicles can be air dried and stored before testing. In addition, membrane vesicles may be packaged more easily in commercial applications than live cells. The use of "non-live" membrane vesicles can be used to detect autoantibodies at a high sensitivity and specificity, whereas live cells need to be fixed for storage and transport which may lead to the loss of the natural conformation of the polypeptide, and also the risk of exposing intracellular epitopes to the antibody (which may reduce the sensitivity or specificity of the assay).

Accordingly, the invention provides a method of detecting in an individual the presence or absence of one or more autoantibodies each directed against an antigen, the method comprising contacting a sample from the individual with a preparation of membrane vesicles comprising the one or more antigens and thereby detecting the presence or absence of the one or more autoantibodies.

The invention also provides:

a method of determining whether or not an individual has or is likely to develop a disease with an autoimmune component, the method comprising detecting the presence or absence of one or more autoantibodies in the individual using a method of the invention, wherein the presence of one or more autoantibodies indicates that the individual has or is likely to develop the disease and wherein the absence of any autoantibodies indicates that the individual does not have or is not likely to develop the disease;

a method of determining whether or not an unborn baby has or is likely to develop a disease with an autoimmune component, the method comprising detecting the presence or absence of one or more autoantibodies in the unborn baby's mother using a method of the invention, wherein the presence of one or more autoantibodies indicates that the unborn baby has or is likely to develop the disease and wherein the absence of any autoantibodies indicates that the unborn baby does not have or is not likely to develop the disease;

a method of treating or preventing a disease with an autoimmune component in an individual or baby who has been determined as having the disease or as likely to develop the disease using a method of the invention, the method comprising administering a therapeutically or prophylactically effective amount of an immunotherapy to the individual or baby and thereby treating or preventing the disease;

a method of treating or preventing a disease with an autoimmune component in an individual or baby, the method comprising (i) determining whether or not the individual or baby has or is likely to develop the disease using a method of the invention, and (ii), if the individual or baby has or is likely to develop the disease, administering a therapeutically or prophylactically effective amount of an immunotherapy to the individual or baby and thereby treating or preventing the disease;

a method of determining whether or not a disease in an individual has an autoimmune component, the method comprising detecting the presence or absence of one or more autoantibodies in the individual using a method of the invention, wherein the presence of one or more autoantibodies indicates the disease has an autoimmune component and wherein the absence of any autoantibodies indicates the disease or condition does not have an autoimmune component;

a method of determining whether or not a disease in an unborn baby has an autoimmune component, the method comprising detecting the presence or absence of one or more autoantibodies in the unborn baby's mother using a method of the invention, wherein the presence of one or more autoantibodies indicates the disease has an autoimmune component and wherein the absence of any autoantibodies indicates the disease does not have an autoimmune component.

a method of treating a disease in an individual or a baby wherein the disease has been determined as having an autoimmune component using a method of the invention, the method comprising administering a therapeutically or prophylactically effective amount of an immunotherapy to the individual or baby and thereby treating or preventing the disease;

a method of treating a disease in an individual or baby, the method comprising (i) determining whether or not the disease has an autoimmune component using a method of the invention, and (ii), if the disease has an autoimmune component, administering a therapeutically or prophylactically effective amount of an immunotherapy to the individual or baby and thereby treating or preventing the disease;

a method of treating or preventing cancer in an individual who has been determined as having cancer or as likely to develop cancer using a method of the invention, the method comprising treating or preventing the cancer in the individual;

a method of treating or preventing cancer in an individual, the method comprising (i) determining whether or not the individual has or is likely to develop cancer using a method of the invention, and (ii), if the individual has or is likely to develop cancer, treating or preventing the cancer in the individual;

a method of determining whether or not an individual with one or more multiple sclerosis (MS)-like symptoms is suitable for MS therapy, the method comprising detecting the presence or absence of one or more autoantibodies in the individual using a method of the invention, wherein the presence of one or more autoantibodies indicates that the individual is not suitable for MS therapy and wherein the absence of any autoantibodies indicates that the individual is suitable for MS therapy; and a kit for detecting in an individual the presence or absence of one or more autoantibodies each directed against an antigen, the kit comprising (a) a preparation of membrane vesicles which comprise the one or more antigens and (b) a solid support to which the membrane vesicles are attached.

DETAILED DESCRIPTION OF THE INVENTION

Figure 1:
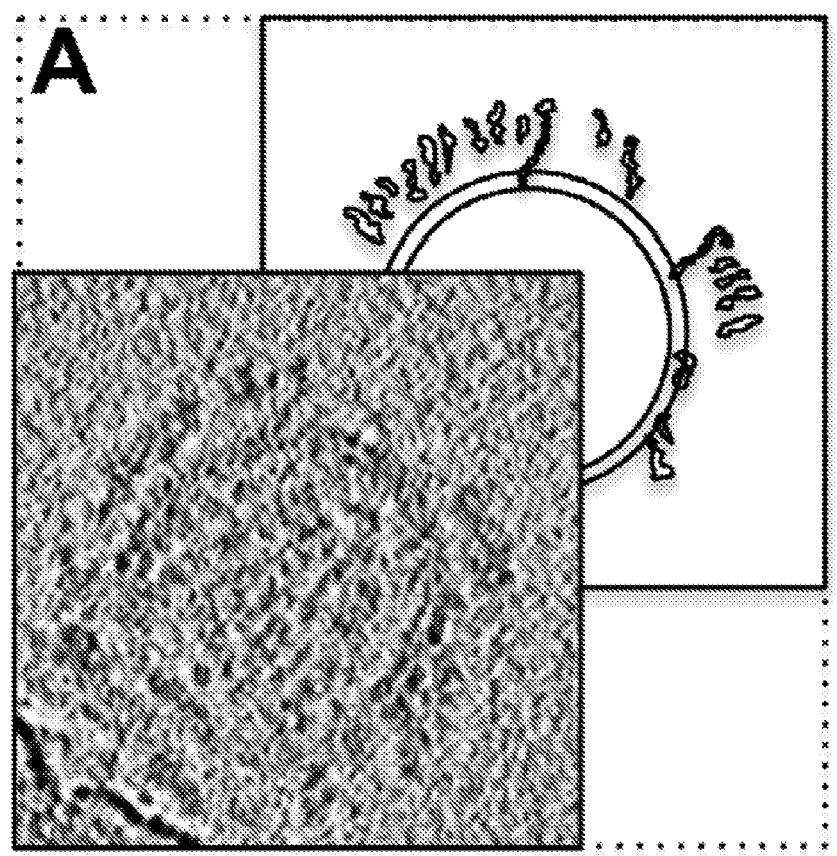
FIG. 1 shows plasma membrane-derived vesicles that comprises a polypeptide antigen on its surface. (A) Cryo-electrotomography (ET) slice and cartoon representation (top right) of a membrane vesicle produced in baby hamster kidney (BHK)-21 cells and comprising receptor protein tyrosine phosphatase sigma (RPTPG) on its surface. This demonstrates that cells transfected with DNA encoding a polypeptide of interest may express high levels of the polypeptide on the surface of the cell, and that the polypeptide may be found on membrane vesicles. The vesicle is ~50 nm in diameter.

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "an autoantibody" includes two or more such autoantibodies, reference to "an antigen" includes two or more such antigens, reference to "a disease" includes two or more such diseases, and the like.

All publications, patents and patent applications cited herein, whether supra or infra, are hereby incorporated by reference in their entirety.

Methods of Detecting Autoantibodies

The present invention relates to a method of detecting in an individual the presence or absence of one or more autoantibodies each directed against an antigen. The invention may concern detecting the presence or absence of one autoantibody. In other words, the invention may concern a uniplex autoantibody assay. The invention may concern detecting the presence or absence of more than one autoantibody, i.e. two or more different autoantibodies. In other words, the invention may concern a multiplex autoantibody assay. In the multiplex assay, each autoantibody is typically directed against a different antigen. In the multiplex assay, each autoantibody may be directed against more than one antigen.

The presence or absence of any number of autoantibodies may be detected using the method of the invention such as 2 or more 3 or more, 4 or more, 5 or more, 10 or more, 20 or more, 30 or more, 40 or more or 50 or more, 100 or more, 1000 or more, or 5000 or more, such as 10,000 or 16,000, autoantibodies can be detected. When detecting more than one autoantibody (i.e. when carrying out a multiplex method), the method typically involves the use of multiple preparations of membrane vesicles each of which comprises a different antigen against which each autoantibody being detected is directed. Any number of preparations of membrane vesicles may be used, such as 2 or more, 3 or more, 4 or more, 5 or more, 10 or more, 20 or more, 30 or more, 40 or more or 50 or more, 100 or more, 1000 or more, or 5000 or more, such as 10,000 or 16,000, preparations. The number of preparations typically corresponds to the number of autoantibodies being detected. Each autoantibody is detected by binding to at least one antigen against. This is discussed in more detail below. In the multiplex method, it is important to be able to distinguish between the binding of the different autoantibodies to the different antigens. This is typically achieved by the position of the different preparations of membrane vesicles (each typically comprising a different antigen) and different and known positions on a solid support. This is discussed in more detail below.

The invention therefore provides a method of detecting the presence or absence of two or more autoantibodies each directed against a different antigen in an individual, the method comprising contacting a sample from the individual with two or more preparations of membrane vesicles each comprising a different antigen and thereby detecting the presence or absence of the two or more autoantibodies.

Alternatively, in the multiplex method, the preparation of membrane vesicles may comprises the same number of different antigens as the number of autoantibodies being detected. Each autoantibody is detected using at least one antigen against which it is directed. This is discussed in more detail below. The invention therefore provides a method of detecting the presence or absence of two or more autoantibodies each directed against a different antigen in an individual, the method comprising contacting a sample from the individual with a preparation of membrane vesicles comprising the different antigens and thereby detecting the presence or absence of the two or more autoantibodies.

Antibodies are usually made to neutralise pathogens by binding to foreign antigens on, for example, viruses or bacteria. Autoantibodies are antibodies that individuals themselves generate against their own antigens (i.e. self antigens) and can cause disease. For example, autoantibodies are typically associated with autoimmune diseases such as those listed below. Autoantibodies to brain and many other antigens have been well characterised (see, for example, Dalmau et. al., Lancet Neurology 2008; Lai et. al., Lancet Neurology 2010; and Irani et. al., Brain 2010), and are found in patients with clinical disease more frequently than in healthy individuals. Autoantibodies may therefore be used to diagnose a disease with an autoimmune component in an individual with a clinical disease, and the treatment of such a disease may comprise reducing the autoantibodies in the individual Autoantibodies may also be generated against biomarkers of diseases, such as cancer biomarkers. Disease biomarkers are typically "self" antigens. Disease biomarkers are typically antigens which are expressed in diseased tissue, but are not expressed in the corresponding normal tissue. Alternatively, disease biomarkers are typically antigens which are expressed in a diseased tissue to a greater extent than in the corresponding normal tissue. If a patient generates autoantibodies against a disease biomarker, such as a cancer biomarker, the disease has an autoimmune component in accordance with the invention. Detection of autoantibodies against disease biomarkers, such as cancer biomarkers, in accordance with the invention may therefore be used to diagnose the disease, such as cancer, in an individual. Although diseases, such as cancer, may have an autoimmune component which allows them to be detected in accordance with the invention, they may not necessarily be treated using immunotherapy. For instance, cancers will likely be treated using typical cancer therapies. This is discussed in more detail below. Similarly, neurological diseases, such as autism, schizophrenia, epilepsy, dementia and psychosis, will also be treated using their typical therapies.

The method of the invention may be carried out on a sample from any individual. The individual is typically one who is suspected of having or is likely to develop an autoimmune disease or for whom treatment using immunotherapy is being considered. For example, an individual who is suspected of having an autoimmune disease may exhibit symptoms of the disease. In other words, the individual may be symptomatic. An individual who is likely to develop an autoimmune disease may be genetically predisposed to produce autoantibodies or genetically predisposed to develop a condition with an autoimmune component, such as an autoimmune disease. However, such an individual may not necessarily exhibit any symptoms of the condition or disease. In other words, the individual may be asymptomatic.

Typically, the individual is human, but alternatively it may be another mammal such as a commercially farmed animal, such as a horse, a cow, a sheep or a pig, or may alternatively be a pet, such as a cat, a dog or a rodent (especially a rat or a mouse), or an experimental animal. The individual is typically a patient.

In a preferred embodiment, the individual is a mother and the presence or absence of one or more autoantibodies in the mother is being used to indicate whether or not her unborn baby (i.e. fetus) has or is likely to develop a disease with an autoimmune component. The unborn baby (i.e. fetus) is typically one who is suspected of having or is likely to develop a disease with an autoimmune component, such as an autoimmune disease. An unborn baby (i.e. fetus) who is likely to develop a disease with an autoimmune component, such as an autoimmune disease, may be genetically predisposed to produce autoantibodies or genetically predisposed to develop a disease with an autoimmune component, such as an autoimmune disease. Although they are detected in the mother, the autoantibodies may be produced by the mother, by the unborn baby or by both the mother and the unborn baby. This aspect of the invention is discussed in more detail below.

The method of the invention comprises contacting a sample from the individual with a preparation of membrane vesicles comprising the one or more antigens and thereby detecting the presence or absence of the one or more autoantibodies.

The sample may be from any tissue or bodily fluid. The sample typically comprises a body fluid and/or cells of the individual and may, for example, be obtained using a needle. The sample may be, or be derived from, plasma, serum, whole blood, urine, saliva, sweat, mucus, tears, lymph, cerebrospinal fluid (CSF), amniotic fluid, milk, faeces or nipple aspirate. Preferably the sample comprises plasma, serum, whole blood or CSF from the individual.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

The method of the invention involves detecting the presence or absence of one or more autoantibodies each directed against an antigen in an individual. In other words, the method involves determining whether or not the one or more autoantibodies are present in the sample. The uniplex method may give a positive result, i.e. where the autoantibody is present in the sample. The uniplex method may alternatively give a negative result, i.e. where the autoantibody is not present in the sample. The multiplex method may give only positive results, i.e. all of the autoantibodies are present, or only negative results, i.e. none of the autoantibodies are present. More likely, the multiplex method may give both positive and negative results, i.e. one or more autoantibodies are present and one or more autoantibodies are absent. If an autoantibody is present, it may also be possible to quantify the autoantibody as discussed in more detail below.

The method typically comprises contacting a sample from the individual with a preparation of membrane vesicles comprising the one or more antigens and detecting whether or not an antibody in the sample binds to each of the one or more antigens and thereby detecting the presence or absence of the one or more autoantibodies. The uniplex method typically comprises contacting a sample from the individual with a preparation of membrane vesicles comprising the antigen and detecting whether or not an antibody in the sample binds to the antigen and thereby detecting the presence or absence of the autoantibody. The multiplex method typically comprises contacting a sample from the individual with two or more preparations of membrane vesicles each comprising a different antigen and detecting whether or not an antibody in the sample binds to each different antigen and thereby detecting the presence or absence of the two or more autoantibodies. The multiplex method may comprise contacting a sample from the individual with a preparation of membrane vesicles comprising the different antigens and detecting whether or not an antibody in the sample binds to each different antigen and thereby detecting the presence or absence of the two or more autoantibodies.

The method preferably comprises detecting whether or not an antibody in the sample binds to each antigen. An antibody binds to an antigen if it binds to the antigen under the conditions of the test and can be detected. The antibody may bind to the antigen to any degree. Methods for measuring binding are discussed below.

The method preferably comprises detecting whether or not an antibody in the sample specifically binds to each antigen. An antibody specifically binds to an antigen if it binds to the antigen with preferential or high affinity, but does not bind or binds with only low affinity to other or different antigens. An antibody binds with preferential or high affinity if it binds with a Kd of $1 \times 10^{-6}$ M or less, more preferably $1 \times 10^{-7}$ M or less, $5 \times 10^{-8}$ M or less, more preferably $1 \times 10^{-8}$ M or less or more preferably $5 \times 10^{-9}$ M or less. An antibody binds with low affinity if it binds with a Kd of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more.

Any method may be used to detect binding or specific binding. Methods of quantitatively measuring the binding of an antibody to an antigen are well known in the art. For example, when an autoantibody specific to the antigen is present in the sample, it may bind or substantially bind with the antigen to form autoantibody-antigen complexes, which may then be detected or quantitatively measured. Binding of an antibody in the sample to the antigen indicates the presence of an autoantibody directed against the antigen in the sample. A lack of binding of an antibody in the sample to the antigen indicates the absence of an autoantibody directed against the antigen in the sample.

Detection of autoantibody-antigen complexes is typically carried out using a secondary antibody which recognises general features common to all antibodies in the individual. For instance, detection of human autoantibody-antigen complexes are typically carried out using a secondary anti-human immunoglobin antibody, typically anti-IgG or anti-human IgM, which recognises general features common to all human IgGs or IgMs respectively. Other Ig classes (IgA, IgD, IgE) can also be detected with appropriate secondary antibodies. The secondary antibody is typically labelled with a detectable label. This facilitates identification of the autoantibody-antigen complex. Any detectable label may be used. Suitable labels include, but are not limited to, fluorescent molecules, luminescent molecules, radioisotopes, e.g. $^{125}$I, $^{35}$S, enzymes, antibodies, antigens, polynucleotides and ligands such as biotin.

For instance, the secondary antibody may be conjugated to an enzyme such as, for example, horseradish peroxidise (HRP), so that detection of an autoantibody/antigen/secondary antibody complex is achieved by addition of an enzyme substrate and subsequent colorimetric, chemiluminescent or fluorescent detection of the enzymatic reaction products, or it may be conjugated to a fluorescent or luminescent signal. Alternatively, the secondary antibody may be labelled with a reporter molecule such as a heavy metal or a radioactive tag. Preferably, the intensity of the signal from the secondary antibody is indicative of the relative amount of the antigen-autoantibody complex in the sample when compared to a positive or negative control, and using different dilutions of the samples.

The binding of antibodies to antigens may be detected by any immunological assay technique, of which many are well known in the art. Examples of suitable techniques include enzyme-linked immunosorbent assay (ELISA), radioimmunoassay, competition assay, inhibition assay, sandwich assay, fluorescent microscopy, microarray or fluorescence-activated cell sorting (FACS) analysis or the like.

The method of detecting the presence or absence of one or more autoantibodies may comprise outputting, optionally on a computer, (i) an indication of whether or not the one or more autoantibodies are present or absent and/or (ii) that the one or more autoantibodies are present or absent and that this indicates whether or not the individual has a disease or is likely to develop a disease with an autoimmune component.

Membrane Vesicles

The method of the invention comprises contacting a sample from an individual with a preparation of membrane vesicles comprising the antigen(s).

Membrane vesicles are small, substantially spherical membrane structures. The membrane vesicles used in the invention are "non-live" or not live. The membrane vesicles are dead.

The membrane vesicles in the preparation are themselves not live cells. The preparation may contain some live cells as discussed below. Live cells typically comprise a nucleus and undergo metabolic and respiratory metabolism. The membrane vesicles in the preparation do not comprise a nucleus. The membrane vesicles may not undergo metabolic and/or respiratory activity.

Membrane vesicles within the preparation may be of different sizes. The membrane vesicles are typically smaller than a typical mammalian cell, which may be, for example, 20 µm in diameter. For example, the membrane vesicles within the preparation may be 2 µm or less in diameter, such as 1 µm or less, 500 nm or less, 300 nm or less, 200 nm or less, 150 nm or less, 100 nm or less or 50 nm or less. The membrane vesicles preferably have a diameter that is sufficient for the one or more antigens to be orientated in their membrane in the same way as in live cells. In this manner, assays utilising membrane vesicles comprising the antigen(s) may be used to detect autoantibodies which are associated with disease pathogenesis. Such autoantibodies bind to extracellular epitopes on an antigen when it is expressed in, or associated with, the cell membrane.

The membrane vesicles may be exosomes. Exosomes are small membrane vesicles typically less than 200 nm in diameter. For example, exosomes typically range in diameter from 10 to 150 nm in diameter, such as from 30 to 90 nm in diameter. Exosomes may be secreted by all mammalian cell types. Exosomes may be naturally occurring at low levels in body fluids such as blood, suggesting a role in cell-cell or organ-organ communication.

The preparation of membrane vesicles used in the method of the invention has preferably been modified, manipulated or processed in such a way that the ratio of the membrane vesicles to cells which produce the membrane vesicles has been increased. The preparation of membrane vesicles used in the method of the invention is not an unmodified or unprocessed population of cells which produces membrane vesicles.

Typically, the membrane vesicles in the preparation are isolated from or substantially isolated from cells. The membrane vesicles may be isolated from or substantially isolated from any cell type that secretes membrane vesicles. Preferably, the preparation of membrane vesicles are isolated from or substantially isolated from mammalian cells such as human cells. More preferably, the preparation of membrane vesicles are isolated or substantially isolated from HEK (human embryonic kidney) cells.

The term "isolated" means that all cells have been removed from the preparation of membrane vesicles. For example, membrane vesicles may be washed from cells to obtain a preparation of membrane vesicles. The preparation preferably does not comprise any cells. The term "substantially isolated" means that the vast majority of cells have been removed from the preparation of membrane vesicles. The preparation preferably comprises a significantly reduced amount of cells compared with an unmodified or unprocessed population of cells which produce membrane vesicles. Any remaining cells may be alive. Any remaining cells are preferably dead.

By way of example, a typical population of HEK cells (at a starting density of $5\times10^5$ cells per ml) may be expected to yield $1\times10^9$ small membrane vesicles (i.e., exosomes) (Andaloussi et al., Nature Protocols, 7, 2112-2126, 2012). As such, a typical HEK cell culture may be expected to yield approximately 2000 membrane vesicles per cell. The membrane vesicles used in the method of the invention are preferably present in a ratio of more than 3000 membrane vesicles per cell, such as more than 4000, more than 5000, more than 6000, more than 7000, more than 8000, more than 9000 or more than 10,000 membrane vesicles per cell. Preferably, the membrane vesicles in the preparation are present in a ratio of more than 50,000, more than 100,000 or more than 1,000,000 membrane vesicles per cell. It is to be understood that the exact values indicated above may differ depending on the type of cell used for membrane vesicle collection, the particular method used to isolate the membrane vesicle from the cells (see below), and the size of membrane vesicle collected.

Methods of isolating membrane vesicles from cultured cells are well known in the art. For example, membrane vesicles may be isolated from cells by centrifugation, for example by differential or ultra-centrifugation. The membrane vesicles are typically present in the supernatant of centrifuged cells. Other methods of isolating membrane vesicles are contemplated by the invention. For example, simplified and shortened processes of membrane vesicle isolation have been developed.

As such, the method of the invention involves the use of a preparation of membrane vesicles that have been isolated from cells. For example, 1 ml of cultured mammalian cells may be expected to yield at least 0.5 µg (microgram), at least 1 µg, at least 2 µg, at least 4 µg at least 6 µg, or at least 8 µg of membrane vesicles such as exosomes.

The membrane vesicles in the preparation may be maintained in a non-dried form (i.e., in a wet form comprising a suitable solution, such as PBS or Hartmann's Solution, or comprising culture medium, such as Dulbecco's Modified Eagle Medium, DMEM) and stored at from 2 to 6° C., typically 4° C. Alternatively, the membrane vesicles in the preparation may be dried. Even when dried to a solid state, the membrane vesicle preparation will typically contain trace amounts of the residual solution or culture medium. Dried membrane vesicles are typically membrane vesicles that comprise less than 50 wt % solvent, such as less than 40 wt % solvent, less than 30 wt % solvent, less than 20 wt % solvent, less than 15 wt % solvent, less than 10 wt % solvent or less than 5 wt % solvent.

As outlined above, membrane vesicles are "non-live" in the sense that they are secreted from "live" cells and do not have characteristics of "live cells" such as a nucleus or metabolic or respiratory activity. As such, membrane vesicles can be dried and are easier to store and handle than live cells.

For example, the preparation of membrane vesicles may be stable under a wide range of temperatures when dried. This allows the preparation of membrane vesicles to be stored at room temperature. Typically, the preparation of membrane vesicles are stored at 4° C. Room temperature is also fine for dried material, but if they had to be transported in solution, they would have to be sterilised and stored at 4 C or below.

The membrane vesicles in the preparation may be attached to a solid support. Examples of suitable solid supports include, but are not limited to, dipsticks, slides, cover slips, membranes and plastic flasks. The membrane vesicles may be maintained in a non-dried form and, for example, spotted onto a support such as a slide shortly before testing. Alternatively, the membrane vesicles in the preparation may be first attached to a solid support and subsequently dried as discussed above.

The membrane vesicles may be attached to the solid support in any manner. For instance, the solid support may be coated with a substance which facilitates attachment of the membrane vesicles. Suitable substances are known in the art and include poly-L-lysine (PLL).

Typically, the preparation of membrane vesicles is spotted onto slides and used in the method of the invention after drying and storage. This allows the transportation of the preparation of membrane vesicles without fixative. This makes it easy to spot the preparation of membrane vesicles onto slides for multiple testing in non-specialist laboratories. This enables the quick diagnosis and treatment of the individual, saving time and cost.

In the method of the invention, the membrane vesicles are preferably derived from cells into which the one or more antigens have been introduced. The introduction, which may be generally referred to as "transformation" or "transfection" may employ any available technique. For eukaryotic cells, suitable transfection techniques may include calcium phosphate transfection, DEAE-Dextran, electroporation, liposome-mediated transfection and transduction using a viral vector. The membrane vesicles are preferably derived from a cell transfected or transformed with the one or more antigens. For example, nucleic acids sequences, expression constructs or vectors which encode the antigen may be introduced into a host cell. In the method of the invention, the membrane vesicles are more preferably derived from a cell which overexpresses the one or more antigens. Overexpression relates to the increased expression of the one or more antigens in a transfected or transformed cell when compared with an untransfected or untransformed cell. Expression of antigens may be measured using known methods, such as western blotting and fluorescent- and colorimetric-based assays.

Typically the host cell secretes, releases or sheds membrane vesicles comprising the antigen into the conditioned medium. In standard methods, this is stimulated using a virus or a chemical vesiculant. Suitable media are known in the art.

Suitable host cells higher eukaryotic cell lines such as mammalian cells. Particular examples of cells which may be modified by insertion of vectors or expression cassettes encoding the antigen include mammalian PC12, HEK293, HEK293A, HEK293T, CHO, BHK-21, HeLa, ARPE-19, RAW264.7 and COS cells. Preferably, the host cell selected will be one which is not only stable, but also allows for mature glycosylation and cell surface expression of the antigen. Preferably, the host cell selected will be one which allows the production of large amounts of membrane vesicles. As such, the host cell typically expresses the construct at a high level. Host cells will be chosen to be compatible with the nucleic acids sequence, expression construct or vector used to transform the cell.

Antigens

The one or more autoantibodies are each directed against an antigen, typically a different antigen. The preparation of membrane vesicles used in the method of the invention comprises the one or more antigens, such as the one or more different antigens, against which the one or more autoantibodies are directed. The preparation of membrane vesicles comprises one antigen against which the autoantibody is directed in the uniplex method and each of the two or more preparations typically comprises one antigen against which the two or more autoantibodies are directed in the multiplex method. Each preparation may comprise two or more antigens against each of which one or more autoantibodies are directed in the multiplex method.

The membrane vesicles comprise the one or more antigens. The membrane vesicles preferably present the one or more antigens on their surfaces. This allows an autoantibody, if present, to bind to its antigen.

Any antigen may be used in the method of the invention. Typically, the one or more antigens are associated with a disease with an autoimmune component, such as an autoimmune disease. Preferably, the one or more antigens are integral membrane proteins, membrane-associated (e.g. GPI anchored proteins), bind to a membrane proteins (e.g. LGI1), or can be modified to be expressed on the cell surface (e.g. LGI1). In some cases, the antigen will be co-expressed with a clustering protein, such as rapsyn for acetylcholine receptors (AChRs) or PSDs for N-Methyl-D-aspartate (NMDA) receptors.

As discussed above, the invention may concern the multiplex detection of two or more autoantibodies, each of which is directed against a different antigen. In such embodiments, the preparation(s) of membrane vesicles comprises the different antigens. Any number of different antigens may be present in the preparation(s), such as 2 or more, 3 or more, 4 or more, 5 or more, 10 or more, 20 or more, 30 or more, 40 or more or 50 or more, 100 or more, 1000 or more, or 5000 or more, such as 10,000 or 16,000, different antigens. The preparation(s) of membrane vesicles typically comprises the same number of different antigens as the number of autoantibodies being detected.

In the multiplex method, it is important to be able to identify which, if any, of the two or more antigens in the preparation of membrane vesicles bind an antibody in the sample. A person skilled in the art is capable of designing an experiment such that the binding of an antibody to each of the antigens can be detected. Typically, the different antigens are located in different positions on a solid support and the binding of an antibody at each position may be detected. This is typically achieved by using two or more preparations of membrane vesicles each of which comprises a different antigen and locating the different preparations in different positions on a solid support. Alternatively, different antigens tagged with different coloured fluorescence may be located together on a solid support and binding of an antibody to each antigen is detected in a different manner.

In the multiplex method, the different antigens are typically present on different preparations of membrane vesicles. In other words, the method may comprise using different preparations of membrane vesicles produced from different cells each of which expresses, preferably overexpresses, one the different antigens. The use of multiple preparations facilitates the positioning of different antigens at different positions on a solid support.

Alternatively, the membrane vesicles in a preparation may comprise more than one of the different antigens. In other words, the preparation may comprise membrane vesicles produced from cells expressing several different antigens.

A method in which some membrane vesicles comprise one antigen and some membrane vesicles comprise more than one antigen is also envisaged. Since membrane vesicle-producing cells normally produce a variety of membrane protein antigens, the membrane vesicles used in the method of the invention typically contain other antigens which are not being used to detect the presence or absence of the one or more autoantibodies.

The one or more antigens may be selected from, but are not limited to in any way, the human polypeptide antigens shown in Table 1 below.

TABLE 1

| Antigens currently relevant to diagnosis of neurological disease | |
|---|---|
| Antigen | NCBI Accession |
| aquaporin-4 (AQP4) | NP_001641.1, NP_004019.1 |
| myelin-oligodendrocyte glycoprotein (MOG) | NP_996537.3, NP_001163889.1, NP_996533.2, NP_001008230.1, NP_001008229.1, NP_996534.2, NP_002424.3, NP_996535.2, NP_996532.2 |
| acetylcholine receptor (AChR) - alpha, beta, gamma, and/or delta subunit(s) | NP_000737.1, NP_001177384.1 |
| acetylcholine receptor (AChR) - beta subunit | NP_000739.1 |
| muscle specific tyrosine kinase (MuSK) | NP_005583.1, NP_001159752.1, NP_001159753.1 |
| contactin associated protein-like 2 (CASPR2) | NP_054860.1 |
| metabotropic glutamate receptor 5 (mGluR5) | NP_001137303.1, NP_000833.1 |
| metabotropic glutamate receptor 1 (mGluR1) | NP_000829.2, NP_001107801.1 |
| N-Methyl-D-aspartate (NMDA) receptor NR1 | NP_000823.4, NP_067544.1, NP_015566.1, NP_001172019.1, NP_001172020.1 |
| N-Methyl-D-aspartate (NMDA) receptor NR2A | NP_001127879.1, NP_000824.1, NP_001127880.1 |
| N-Methyl-D-aspartate (NMDA) receptor NR2B | NP_000825.2 |
| leucine-rich glioma inactivated protein 1(LGI1) | NP_005088.1 |
| Contactin-2 (CNTN2) | NP_005067.1 |
| glutamic acid decarboxylase 1 (GAD1) | NP_038473.2, NP_000808.2 |
| glutamic acid decarboxylase 2 (GAD2) | NP_001127838.1, NP_000809.1 |
| AMPA glutamate receptor 1 (GluA1) | NP_000818.2, NP_001107655.1, NP_001244948.1, NP_001244949.1, NP_001244950.1, NP_001244951.1, NP_001244952.1 |
| AMPA glutamate receptor 2 (GluA2) | NP_000817.2, NP_001077088.1, NP_001077089.1 |
| AMPA glutamate receptor 3 (GluA3) | NP_015564.4, NP_000819.3, NP_001243672.1 |
| GABA type B receptor subunit 1(GABABR1) | NP_001461.1, NP_068703.1, NP_068704.2 |
| GABA receptor type B receptor subunit 2 (GABABR2) | NP_005449.5 |
| Glycine receptor alpha 1(GlyRA1) | NP_000162.2, NP_001139512.1 |
| Glycine receptor alpha 2(GlyRA2) | NP_002054.1, NP_001112357.1, NP_001112358.1, NP_001165413.1 |
| Glycine receptor alpha 3 (GlyRA3) | NP_006520.2, NP_001036008.1 |
| Glycine receptor alpha 4 (GlyRA4) | NP_001019623.2, NP_001165756.1 |
| Glycine receptor beta (GlyB) | NP_000815.1, NP_001159532.1, NP_001159533.1 |
| Voltage-gated calcium channel (VGCC) | NP_000713.2, NP_954856.1, NP_954855.1, NP_000714.3, NP_001193846.1, NP_001193845.1, NP_000716.2, NP_060868.2, NP_001139270.1, NP_001005747.1, NP_000717.2, NP_001005746.1, NP_001005505.1, NP_001167522.1, NP_758952.4, NP_006021.2 |
| Receptor protein tyrosine phosphatase sigma (RPTPσ) | NP_002841.3, NP_570924.2, NP_570923.2, NP_570925.2 |

The method of the invention may include the use of one or more of the antigens listed above. For example, the preparation of membrane vesicles may comprise AQP4 and MOG antigens. In other words, it may be clinically useful to detect in parallel autoantibodies directed against AQP4 and MOG. The preparation of membrane vesciles may comprise all of the antigens listed above in Table 1. The invention therefore may provide a multiplex assay which is capable of determining whether or not an individual is producing autoantibodies directed against any of the antigens listed in Table 1 above. In such an assay, the presence or absence of an autoantibody directed against each antigen may be distinguished. A person skilled in the art is capable of designing other multiplex assays in accordance with the invention.

The polypeptide sequences of the antigens listed above are identified by NCBI accession numbers. For some antigens, multiple NCBI accession numbers are indicated which relate to different isoforms of the respective antigens. The method of the invention may involves the use of variants of these polypeptide sequences, which are capable of binding to an autoantibody. For example, the method of the invention may use sequences which have at least 95%, at least 98% or at least 99%, homology to any one of the polypeptide sequences identified in Table 1 based on amino acid identity over their entire sequence and which are capable of binding to an autoantibody.

The above mentioned homology is calculated on the basis of amino acid identity (sometimes referred to as "hard homology"). The UWGCG Package provides programs including GAP, BESTFIT, COMPARE, ALIGN and PILEUP that can be used to calculate homology or line up sequences (for example used on their default settings). The BLAST algorithm can also be used to compare or line up two sequences, typically on its default settings. Software for performing a BLAST comparison of two sequences is publicly available through the National Center for Biotechnology Information (http://www.ncbi.nlm.nih.gov/). This algorithm is further described below. Similar publicly available tools for the alignment and comparison of sequences may be found on the European Bioinformatics Institute website (http://www.ebi.ac.uk), for example the ALIGN and CLUSTALW programs.

A BLAST analysis is preferably used for calculating identity. Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequences typically differ by at least 1, 2, 5, 10, 20 or more mutations (which may be substitutions, deletions or insertions of amino acids). These mutations may be measured across any of the regions mentioned above in relation to calculating identity. The substitutions are preferably conservative substitutions. These are defined according to the following Table. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Any of the one or more of the antigens used in the method of the invention may be in the form of a dimer or a larger array. For example, AQP4 is known to form in a tetramer and then becomes clustered to higher order arrays, and AChR can be clustered using the scaffold protein rapsyn to form large arrays of tightly packed receptors. Any of the one or more of the antigens used in the method of the invention may be further chemically-modified to form a derivative. Derivatives include polypeptides that have lipid extensions or have been glycosylated. Derivatives also include polypeptides that have been detectably labelled. Detectably labelled polypeptides have been labelled with a labelling moiety that can be readily detected. Examples of labelling moieties include, but are not limited to, radioisotopes or radionucleotides, fluorophores such as green fluorescent protein (GFP), electron-dense reagents, quenchers of fluorescence, enzymes, affinity tags and epitope tags. Preferred radioisotopes include, but are not limited to, tritium and iodine. Affinity tags are labels that confer the ability to specifically bind a reagent onto the labelled molecule. Examples include, but are not limited to, biotin, histidine tags and glutathione-S-transferase (GST). Labels may be detected by, for example, spectroscopic, photochemical, radiochemical, biochemical, immunochemical or chemical methods that are known in the art.

Any of the one or more antigens used in the method of the invention may comprise a mutation that is associated with a disease with an autoimmune component. The method of the invention may also use one or more antigens derived from the individual being tested.

Any of the one or more antigens used in the method of the invention may also comprise additional amino acids or polypeptide sequences. Any of the one or more antigens used in the method of the invention may comprise additional polypeptide sequences such that they form fusion proteins. The additional polypeptide sequences may be fused at the amino terminus, carboxy terminus or both the amino terminus and the carboxy terminus. Alternatively, the additional polypeptide sequence may be within the coding region of the polypeptide. Examples of fusion partners include, but are not limited to, GST, maltose binding protein, alkaline phosphatates, thiorexidin, GFP,biotin tags, histidine tags and epitope tags (for example, Myc or FLAG). CCRL2 polypeptides may be fused to a GTP-binding protein (G protein).

For example, an antigen may be an intracellular protein, and may further comprise additional polypeptide sequences to direct it to the membrane surface of the cell. Examples of fusion partners to direct the antigen to the cell surface are well known in the art. Directing the antigen to the membrane surface of the cell in this manner may lead to an increased concentration of antigen in the preparation of membrane vesicles used in the method of the invention.

As outlined above, cells which produce membrane vesicles may be transfected or transformed with polynucleotide sequences that encode the one or more antigens. For example, mammalian cells may be transfected with polynucleotide sequences that encode any one of the polypeptide sequences identified in Table 1, or additional isoforms or variants thereof. Polynucleotide sequences may be isolated and replicated using standard methods in the art. The gene encoding the antigen may be amplified using PCR involving specific primers. The amplified sequences may then be incorporated into a recombinant replicable vector such as a cloning vector. The vector may be used to replicate the polynucleotide in a compatible host cell. Thus polynucleotide sequences encoding the antigen may be made by introducing a polynucleotide encoding the antigen into a replicable vector, introducing the vector into a compatible host cell, and growing the host cell under conditions which bring about replication of the vector. The vector may be recovered from the host cell. Suitable host cells are described above.

The polynucleotide sequence may be cloned into any suitable expression vector. In an expression vector, the polynucleotide sequence encoding a construct is typically operably linked to a control sequence which is capable of providing for the expression of the coding sequence by the host cell. Such expression vectors can be used to express a construct.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotides, may be introduced into the vector.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example an ampicillin resistance gene. Promoters and other expression regulation signals may be selected to be compatible with the host cell for which the expression vector is designed. For example, a cytomegalovirus (CMV) or chicken-beta-actin promoter may be typically used for constitutive expression of the polypeptide in mammalian cell lines.

Typically, the membrane vesicles are derived from a cell transfected with the antigen, wherein the cell overexpresses the polynucleotide encoding the antigen. Increased levels of the antigen in the cell may lead to an increased level of the antigen in the preparation of membrane vesicles.

Diseases with an Autoimmune Component

In a method of the invention, the presence of one or more autoantibodies in the individual may indicate that the individual has or is likely to develop a disease with an autoimmune component. Similarly, the absence of any autoantibodies in the individual may indicate that the individual does not have or is not likely to develop a disease with an autoimmune component.

In a method of the invention, the individual may be a mother and the presence of one or more autoantibodies in the mother may indicate that her unborn baby (i.e. fetus) has or is likely to develop a disease with an autoimmune component. Similarly, the absence of any autoantibodies in the mother may indicate that her unborn baby (i.e. fetus) does not have or is not likely to develop a disease with an autoimmune component. The autoantibodies may be produced by the mother, by the unborn baby or by both the mother and the unborn baby.

The phrase "has a disease with an autoimmune component" means that the individual or unborn baby (i.e. fetus) has already developed the disease, such as one of the diseases outlined below. For example, the individual or unborn baby (i.e. fetus) may exhibit clinical features of the disease. Clinical features of particular diseases with an autoimmune component are indicated in Table 2 of the Example.

The phrase "likely to develop a disease with an autoimmune component" means that the individual or unborn baby (i.e. fetus) is at risk of or has an increased risk of developing a disease with an autoimmune component. Such an individual or unborn baby (i.e. fetus) typically does not exhibit symptoms of the disease. Such an individual or unborn baby (i.e. fetus) may however be monitored further for possible development of the symptoms of the disease.

The phrase "does not have a disease with an autoimmune disease" means that the individual or unborn baby (i.e. fetus) has not developed a disease with an autoimmune component, such as one of the diseases outlined above. The individual or unborn baby (i.e. fetus) typically does not exhibit symptoms of the disease.

The phrase "not likely to develop a disease with an autoimmune component" typically means that the individual or unborn baby (i.e. fetus) is not at risk of or has a decreased risk of developing a disease with an autoimmune component.

The invention also provides a method of determining whether or not an individual or unborn baby (i.e. fetus) has or is likely to develop a disease with an autoimmune component, comprising detecting the presence or absence of one or more autoantibodies using the method of the invention. In other words, the method of the invention may concern the diagnosis or prognosis of any disease with an autoimmune component. The method of the invention may concern determining whether or not an individual or unborn baby (i.e. fetus) is at risk of or has an increased risk of developing a disease with an autoimmune component.

The disease with an autoimmune component may be any disease that involves an autoimmune response and the production of autoantibodies. The disease may be a disease or condition resulting from the presence of the autoantibody during development, such as arthrogryposis (i.e. fixed joint contractures), autism or schizophrenia. The disease is typically an autoimmune disease.

Preferably, the disease with an autoimmune component is selected from myasthenia gravis (MG), Lambert Eaton myasthenic syndrome, acquired neuromyotonia, limbic encephalitis, NMDAR-antibody encephalitis, cerebellar ataxia, stiff person syndrome, progressive encephalomyelitis with rigidity and myoclonus, demyelinating inflammatory disorders, neuromyelitis optica, acute disseminated encephalomyelitis (ADEM), type 1 diabetes mellitus, rheumatoid arthritis, autoimmune thyroiditis, inflammatory bowel disease, bullous pemphigoid, Morvan's syndrome, neuromyotonia, arthrogryposis (i.e. fixed joint contractures), autism, schizophrenia, epilepsy, dementia or psychosis. Alternatively, the disease with an autoimmune component may be cancer or associated with cancer.

The disease with an autoimmune component in an unborn baby is preferably an autoimmune disease or a disease or condition resulting from the presence of the autoantibody during development, such as arthrogryposis (i.e. fixed joint contractures), autism or schizophrenia. Although babies can develop the same autoimmune disease as their mothers, they can also develop developmental diseases due to the presence of an antibody that alters their development. For instance, a condition due to altered brain development, such autism or schizophrenia, may result from the presence of autoantibodies from the mother. It is accepted (although not common) that maternal antibodies against fetal AChR can cause longer lasting damage to the baby by paralysing its muscles in utero resulting in arthrogryposis (fixed joint contractures). This can be fatal or lead to disabilities at birth and later. The antibodies tend to disappear within a few months at most but leave the damage. There is also the hypothesis, being tested by some groups in the USA, that maternal antibodies to fetal brain antigens, for instance, can cause neurodevelopmental diseases, such as autism or schizophrenia.

Methods of Treating a Disease with an Autoimmune Component

The present invention also provides a method of treating or preventing a disease with an autoimmune component in an individual or baby who has been determined as having the disease or as likely to develop the disease using the method of the invention, comprising administering a therapeutically or prophylactically effective amount of an immunotherapy to the individual or baby and thereby treating or preventing the disease. The baby is typically treated after it is born. Suitable immunotherapies include, but are not limited to, corticosteroids, intravenous immunoglobulins, plasma exchange, steroid-sparing drugs (e.g. Azathioprine, mycophenolate mofetil), cyclophosphamide, cyclosporine and therapeutic monoclonal antibodies such as Rituxan and eculizumab.

The invention also provides a method of treating or preventing a disease with an autoimmune component in an individual or baby, comprising (i) determining whether or not an individual or unborn baby has or is likely to develop the disease using the method described above, and, (ii) if the individual or unborn baby has or is likely to develop the disease, administering a therapeutically or prophylactically effective amount of an immunotherapy to the individual or baby and thereby treating or preventing the disease. The baby is typically treated after it is born.

The diseases with an autoimmune component may be any of those described above.

The dose of immunotherapy to be used in accordance with the invention will depend upon the nature of the specific therapy. A suitable dose can be determined by a skilled practitioner based on his common general knowledge, taking into account, for example, the regime and dose that would be used for in vivo treatment using that therapy. For example, a suitable dose may be selected to reflect the level of a therapeutic agent that would be present in the blood circulatory system of an individual or baby after in vivo administration.

The method may be for treating the disease. In the case of treating, the individual or baby typically has the disease, i.e. has been diagnosed as having the disease, or is suspected as having the disease, i.e. shows the symptoms of the disease. As used herein, the term "treating" includes any of following: the prevention of the disease or of one or more symptoms associated with the disease; a reduction or prevention of the development or progression of the disease or symptoms; and the reduction or elimination of an existing disease or symptoms.

The method may be for preventing the disease. In the case of prevent, the individual or baby is typically likely to develop the disease or is at risk of developing the disease. In this embodiment, the individual or baby can be asymptomatic. The individual or baby can have a genetic predisposition to the disease with an autoimmune component. The individual or baby may have one or more family members with the disease with an autoimmune component. As used herein, the term "preventing" includes the prevention of the onset of the disease or of one or more symptoms associated with the disease.

Therapy and prevention includes, but is not limited to, preventing, alleviating, reducing, curing or at least partially arresting symptoms and/or complications resulting from or associated with the disease with an autoimmune component. When provided therapeutically, the therapy is typically provided at or shortly after the onset of a symptom of the disease. Such therapeutic administration is typically to prevent or ameliorate the progression of, or a symptom of the disease or to reduce the severity of such a symptom or disease. When provided prophylactically, the treatment is typically provided before the onset of a symptom of disease (as above). Such prophylatic administration is typically to prevent the onset of symptoms of the disease.

Specific routes, dosages and methods of administration of immunotherapies may be routinely determined by the medical practitioner. Typically, a therapeutically effective or a prophylactically effective amount of the immunotherapy is administered to the individual or baby. A prophylactically effective amount is an amount which prevents the onset of one or more symptoms of the disease. A therapeutically effective amount of the immunotherapy is an amount effective to ameliorate one or more symptoms of the disease. A therapeutically effective amount of the immunotherapy is preferably an amount effective to abolish one or more of, or preferably all of, the symptoms of the disease.

The immunotherapy may be employed alone as part of a composition, such as but not limited to a pharmaceutical composition or a vaccine composition or an immunotherapeutic composition to prevent and/or treat the disease with an autoimmune component.

The immunotherapy may be used in combination with one or more other therapies intended to treat the same individual or baby. By a combination is meant that the therapies may be administered simultaneously, in a combined or separate form, to an individual or baby. The therapies may be administered separately or sequentially to an individual or baby as part of the same therapeutic regimen. For example, an immunotherapy may be used in combination with another therapy intended to treat an inflammatory or autoimmune disease. The other therapy may be a general therapy aimed at treating or improving the condition of an individual or baby with an inflammatory or autoimmune disease. For example, treatment with methotrexate, glucocorticoids, salicylates, nonsteroidal anti-inflammatory drugs (NSAIDs), analgesics, other DMARDs, aminosalicylates, corticosteroids, and/or immunomodulatory agents (e.g., 6-mercaptopurine and azathioprine) may be combined with an immunotherapy. The other therapy may be a specific treatment directed at the particular disease or condition suffered by the individual or baby, or directed at a particular symptom of such a disease or condition.

The immunotherapy may be administered to the individual or baby by any suitable means. The immunotherapy can be administered by enteral or parenteral routes such as via oral, buccal, anal, pulmonary, intravenous, intra-arterial, intramuscular, intraperitoneal, intraarticular, topical or other appropriate administration routes.

The formulation will depend upon factors such as the nature of the immunotherapy and the disease to be treated. The immunotherapy may be administered in a variety of dosage forms. It may be administered orally (e.g. as tablets, troches, lozenges, aqueous or oily suspensions, dispersible powders or granules), parenterally, subcutaneously, intravenously, intramuscularly, intrasternally, transdermally or by infusion techniques. The immunotherapy may also be administered as a suppository. A physician will be able to determine the required route of administration for each particular individual or baby.

Typically, the immunotherapy is formulated for use with a pharmaceutically acceptable carrier or diluent and this may be carried out using routine methods in the pharmaceutical art. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous or infusions may contain as carrier, for example, sterile water or preferably they may be in the form of sterile, aqueous, isotonic saline solutions.

For suppositories, traditional binders and carriers may include, for example, polyalkylene glycols or triglycerides; such suppositories may be formed from mixtures containing the active ingredient in the range of 0.5% to 10%, preferably 1% to 2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the pharmaceutical composition is lyophilised, the lyophilised material may be reconstituted prior to administration, e.g. a suspension. Reconstitution is preferably effected in buffer.

Capsules, tablets and pills for oral administration to an individual or baby may be provided with an enteric coating comprising, for example, Eudragit "S", Eudragit "L", cellulose acetate, cellulose acetate phthalate or hydroxypropylmethyl cellulose.

Pharmaceutical compositions suitable for delivery by needleless injection, for example, transdermally, may also be used.

A therapeutically or prophylactically effective amount of the compound is administered. The dose may be determined according to various parameters, especially according to the compound used; the age, weight and condition of the individual or baby to be treated; the route of administration; and the required regimen. Again, a physician will be able to determine the required route of administration and dosage for any particular individual or baby. A typical daily dose is from about 0.1 to 50 mg per kg, preferably from about 0.1 mg/kg to 10 mg/kg of body weight, according to the activity of the specific inhibitor, the age, weight and conditions of the individual or baby to be treated, the type and severity of the disease and the frequency and route of administration. Preferably, daily dosage levels are from 5 mg to 2 g.

Method of Determining Whether or Not a Disease in an Individual or Baby Has an Autoimmune Component The invention provides a method of determining whether or not a disease in an individual has an autoimmune component, comprising detecting the presence or absence of one or more autoantibodies in the individual using the method of the invention, wherein the presence of one or more autoantibodies indicates the disease has or is likely to have an autoimmune component and wherein the absence of any autoantibodies indicates the disease does not have or is not likely to have an autoimmune component. The invention also provides a method of determining whether or not a disease in unborn baby (i.e. fetus) has an autoimmune component, comprising detecting the presence or absence of one or more autoantibodies in the unborn baby's mother using the method of the invention, wherein the presence of one or more autoantibodies indicates the disease has or is likely to have an autoimmune component and wherein the absence of any autoantibodies indicates the disease does not have or is not likely to have an autoimmune component. As discussed above, a disease has an autoimmune component if the individual or unborn baby (i.e. fetus) generates autoantibodies that are associated with the disease.

The disease may be any disease. For example, the disease may be of the blood and blood-forming organs; of the circulatory system; of the digestive system; of the genitourinary system; of the musculoskeletal system and connective tissue; of the nervous system and sense organs; of the respiratory system; or of the skin and subcutaneous tissue. The disease may be an endocrine, immune, nutritional or metabolic disease. The disease may be a mental disorder or a parasitic disease. The disease may be secondary to a cancer or the disease may be a cancer. The individual has the disease and so is typically symptomatic.

The invention also provides a method of treating a disease in an individual or baby wherein the disease has been determined as having an autoimmune component using the method described above, comprising administering a therapeutically or prophylactically effective amount of an immunotherapy to the individual or baby and thereby treating or preventing the disease. The baby is typically treated after it is born.

Further provided is a method of treating a disease in an individual or baby, comprising (i) determining whether or not the disease has an autoimmune component using the method described above and, (ii) if the disease has an autoimmune component, administering a therapeutically or prophylactically effective amount of an immunotherapy to the individual or baby and thereby treating or preventing the disease. The baby is typically treated after it is born.

Immunotherapies are described above.

Method of Treating Cancer

The invention also provides a method of treating or preventing cancer in an individual who has been determined as having cancer or as likely to develop cancer using a method of the invention. As discussed above, the invention may be used to detect autoantibodies against cancer biomarkers. In the method of the invention, the presence of one or more autoantibodies against one or more cancer biomarkers in the individual may indicate that the individual has or is likely to develop cancer. Similarly, the absence of any autoantibodies against any cancer biomarkes in the individual may indicate that the individual does not have or is not likely to develop cancer.

The method comprises treating or preventing the cancer in the individual. The cancer may be treated or prevented using any standard cancer therapies. The cancer may be treated with chemotherapy, radiation therapy, surgery or a combination thereof. The discussion above concerning treatment and prevention of diseases equally applies to these embodiments.

The invention also provides a method of treating or preventing cancer in an individual, which comprises (i) determining whether or not the individual has or is likely to develop cancer using a method of the invention, and (ii), if the individual has or is likely to develop cancer, treating or preventing the cancer in the individual.

Suitability for Multiple Sclerosis (MS) Therapy

Treatment with MS therapy may cause disease exacerbation in patients misdiagnosed with MS, and instead having a different autoimmune disease.

The invention therefore further provides a method of determining whether or not an individual with multiple sclerosis (MS)-like symptoms is suitable for MS therapy, comprising detecting the presence or absence of one or more autoantibodies in the individual using the method of the invention, wherein the presence of one or more autoantibodies indicates that the individual is not suitable for MS therapy and wherein the absence of any autoantibodies indicates that the individual is suitable for MS therapy.

Typically, the antigen that is used to detect the presence or absence of the autoantibody is Aquaporin-4 (AQP4) and/or myelin-oligodendrocyte glycoprotein (MOG). Typically the MS-like symptoms are selected from vision problems, balance problems and dizziness, fatigue, bladder problems, mobility problems, stiffness and/or spasms.

Typically, the MS therapy is selected from Beta interferon, glatiramer acetate Tysabri and Gilenya. Individuals may be as defined above.

Kits

The invention provides an assay kit for detecting in an individual the presence or absence of one or more autoantibodies each directed against an antigen. The kit comprises (a) a preparation of membrane vesicles which comprise the one or more antigens and (b) a solid support to which the membrane vesicles are attached.

Preferably, the kit comprises instructions to use the kit, preferably in the method of the invention. Preferably, the kit also comprises means for contacting the preparation of membrane vesicles with a sample from the individual. The kit preferably further comprises a secondary antibody which is capable of binding to the one or more autoantibodies and/or a detectable label. The secondary antibody is preferably labelled with the detectable label. Suitable detectable labels are discussed above. The preparation of membrane vesicles in the kit may be as defined above.

The invention is illustrated by the following Example.

EXAMPLE

1. Introduction

The advantage of existing "cell-based" assays (as described above) to detect autoantibodies are three fold: the antigen is expressed is a native conformation on the cell surface, as it is in vivo; in some cases the antigen can be clustered by co-transfection with intracellular scaffold proteins, in order to enhance antibody binding (Leite et al., Brain 2008); and because the cells are not fixed or permeabilised, only antibodies that bind the extracellular epitopes of the antigen are detected.

For example, LGI1 and CASPR2 assays may be used to create slides of the relevant cells for detection of the antibodies. However, for this purpose, and for transport, cells need to be first fixed and this interferes with the conformation of the antigen and permeabilises the cells, and means that antibodies in the human sample that bind to intracellular epitopes (which are unlikely to be pathogenic) or to other intracellular proteins can also be detected. Although the microchip technique does have the advantage that multiple antigens can be tested at one time—which is important for future diagnostics—these assays are not sufficiently reliable and sensitive for optimal clinical services. Moreover, the glass slides used are heavy and the transport costs are a definite problem for many centres worldwide.

2. Method

Figure 2:
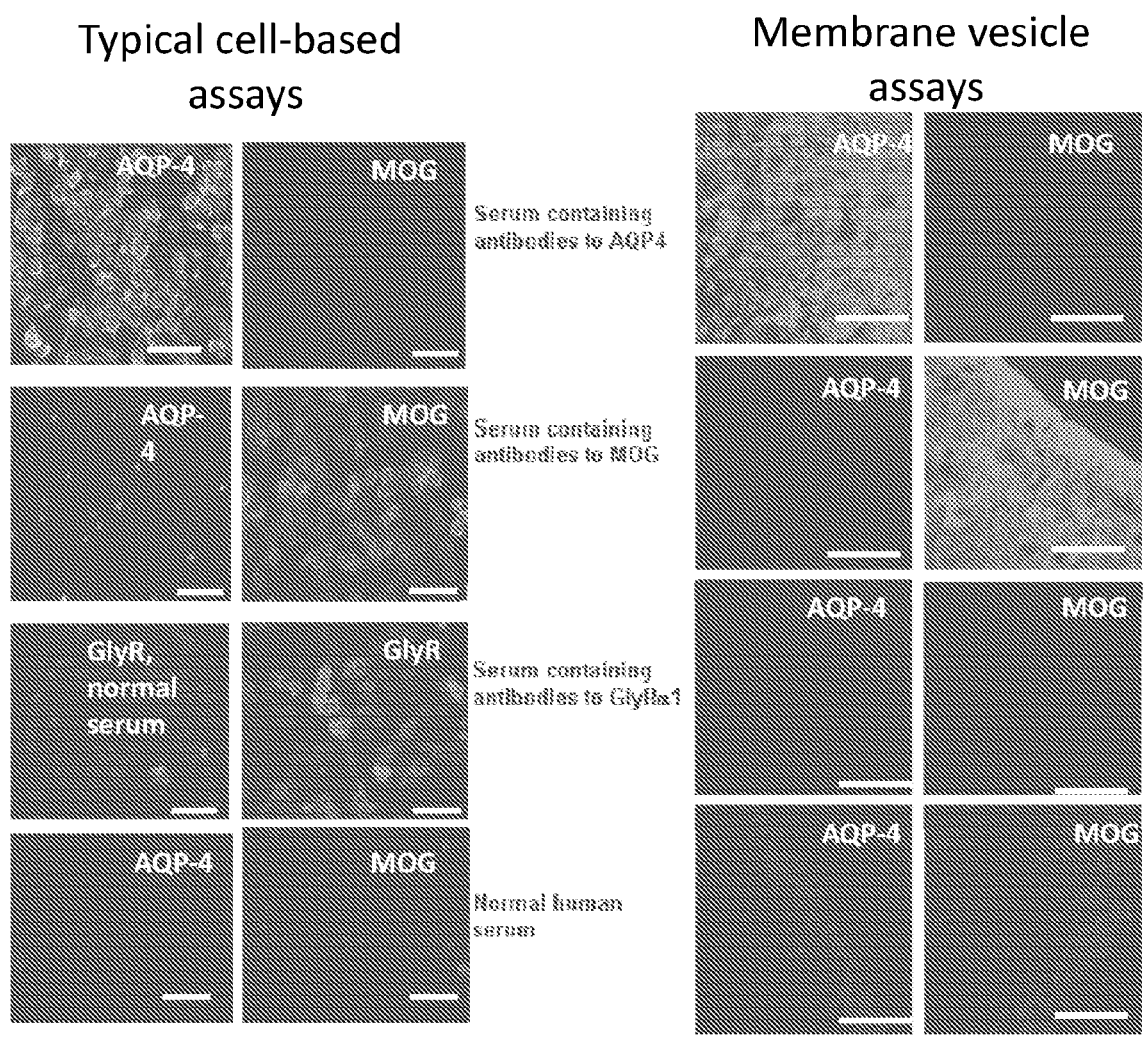
FIG. 2 shows at lower power the binding of patients' antibodies to HEK cells (left hand panels) or HEK cell membrane vesicles (right hand panels) detected by Alexa fluor-568 (red) labelled anti-human IgG. The top row shows the presence of antibodies in the serum from a patient with neuromyelitis optica (NMO) binding to HEK cells hat have been transiently transfected with DNA encoding human M23 aquaporin-4 (AQP4, left) or membrane vesicles prepared from the AQP4-expressing HEK cells (right). The same serum does not bind to HEK cells or membrane vesicles prepared from HEK cells that have been transiently transfected with DNA for myelin-oligodendrocyte glycoprotein (MOG), indicating the presence of AQP4 specific antibodies in the patient's serum. Similarly, the presence of antibodies to MOG in another patient's serum are detected with no binding to the AQP4 HEK cells or membrane vesicles (second row from top). The third and fourth rows from top show serum from a normal healthy individual or patient with glycine receptor antibodies binding to HEK cells expressing GlyR alpha1 (left) but not to membrane vesicles from HEK cells expressing AQP4 or MOG (right), and serum from a normal healthy individual that do not bind to glycine receptors or either antigen. For the left panels, HEK cells were grown on coated glass slides and transfected with the appropriate DNA. The cells were cultured for 24 hours, washed, and after another 24 hours at 37 C, the sera were applied to the live cells and then washed before fixing and determination of bound IgG. For the right panels, membrane vesicles prepared from similarly transfected HEK cells were spotted onto coated glass slides and left to dry overnight before application of the sera. Scale bar: 10 nm (A) and 1 µm (B-E).
Figure 3:
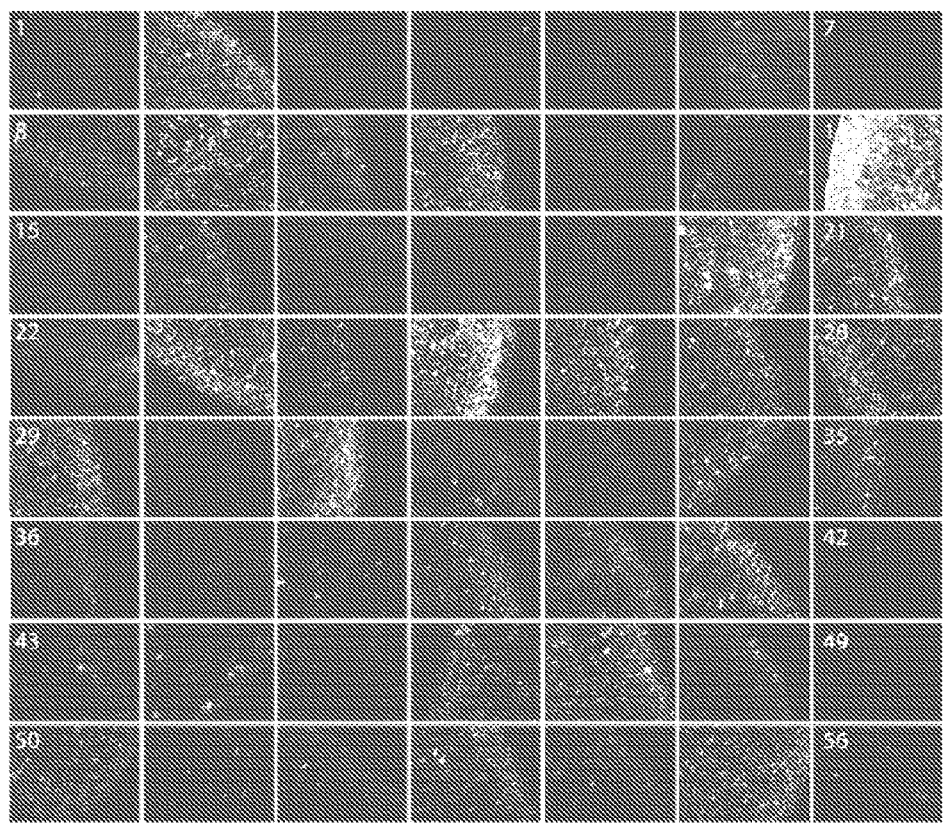
FIG. 3 shows examples of testing 80 sera from patients and controls for AQP4-antibodies. All scoring was performed blinded and reported before unblinding and comparing with the cell-based assay scores.
Figure 4:
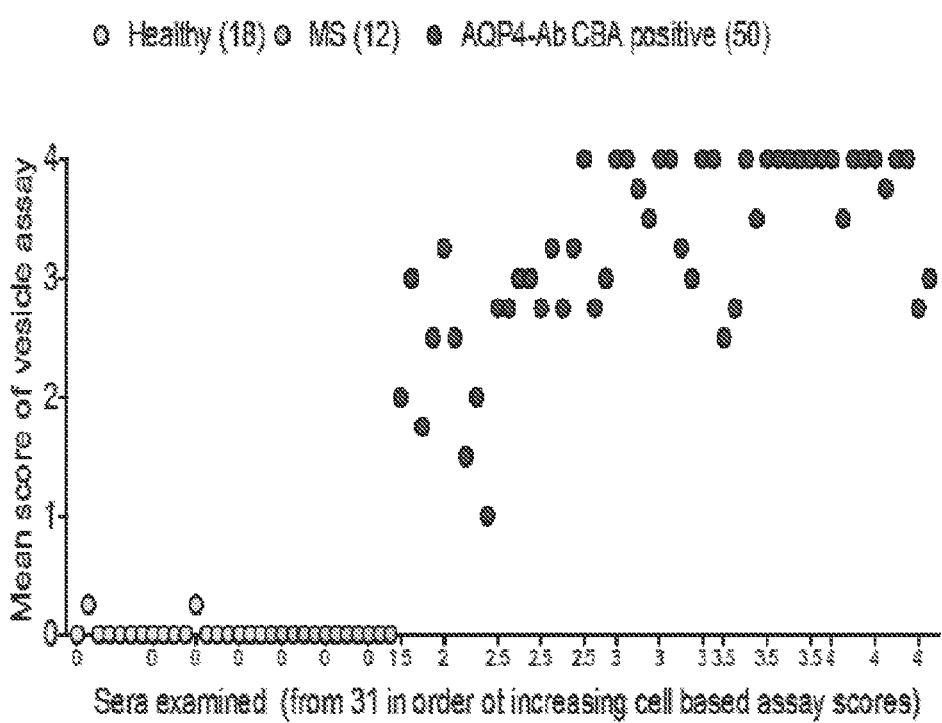
FIG. 4 shows the results from FIG. 3 re-ordered to show the vesicle assay results of 18 healthy control sera, 12 multiple sclerosis (MS) sera and 50 AQP4-Ab positive sera. All results were reported before unblinding. None of the controls (healthy or MS) reach a threshold score of 1. All of the AQP4-Ab positive sera give scores of 1 or over. Thus, the assay for AQP4 antibodies is specific and sensitive.
Figure 5A:
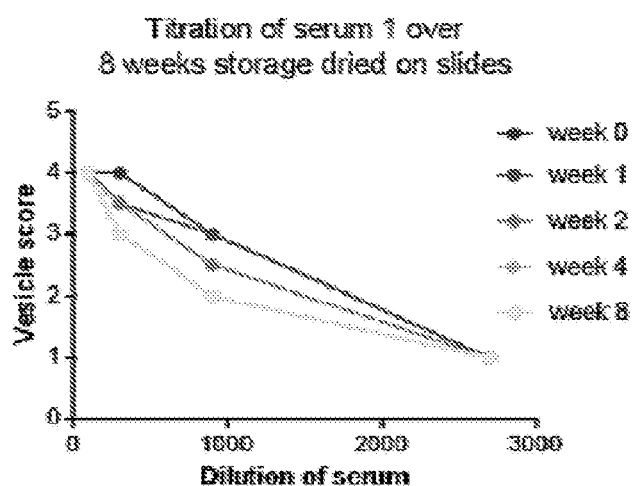
FIG. 5A and FIG. 5B show the results of a single serum tested at different dilutions of serum at different time points from 0 to 8 weeks. The serum scores 4 at starting dilution of 1:100 and 1 at final dilution of 1:2700 dilution. There is no clear difference between the results when the vesicles are stored in buffer and applied to slides at the time (A) or stored already applied and dried (B). However, when comparing the results at weeks 0 and 4 for six AQP4-Ab positive sera with different titres, the buffer storage appeared to give better results (C). Nevertheless, the results were still positive under either condition.
Figure 5B:
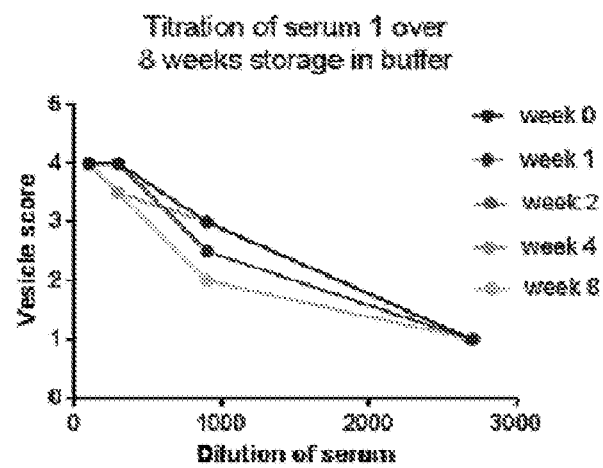
Figure 5C:
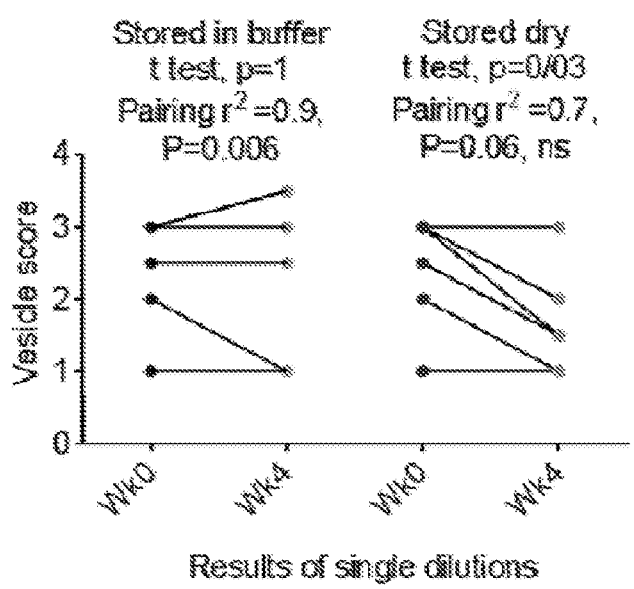
FIG. 5 shows that the AQP4-expressing vesicles can be stored either dry or in buffer.
Figure 6:
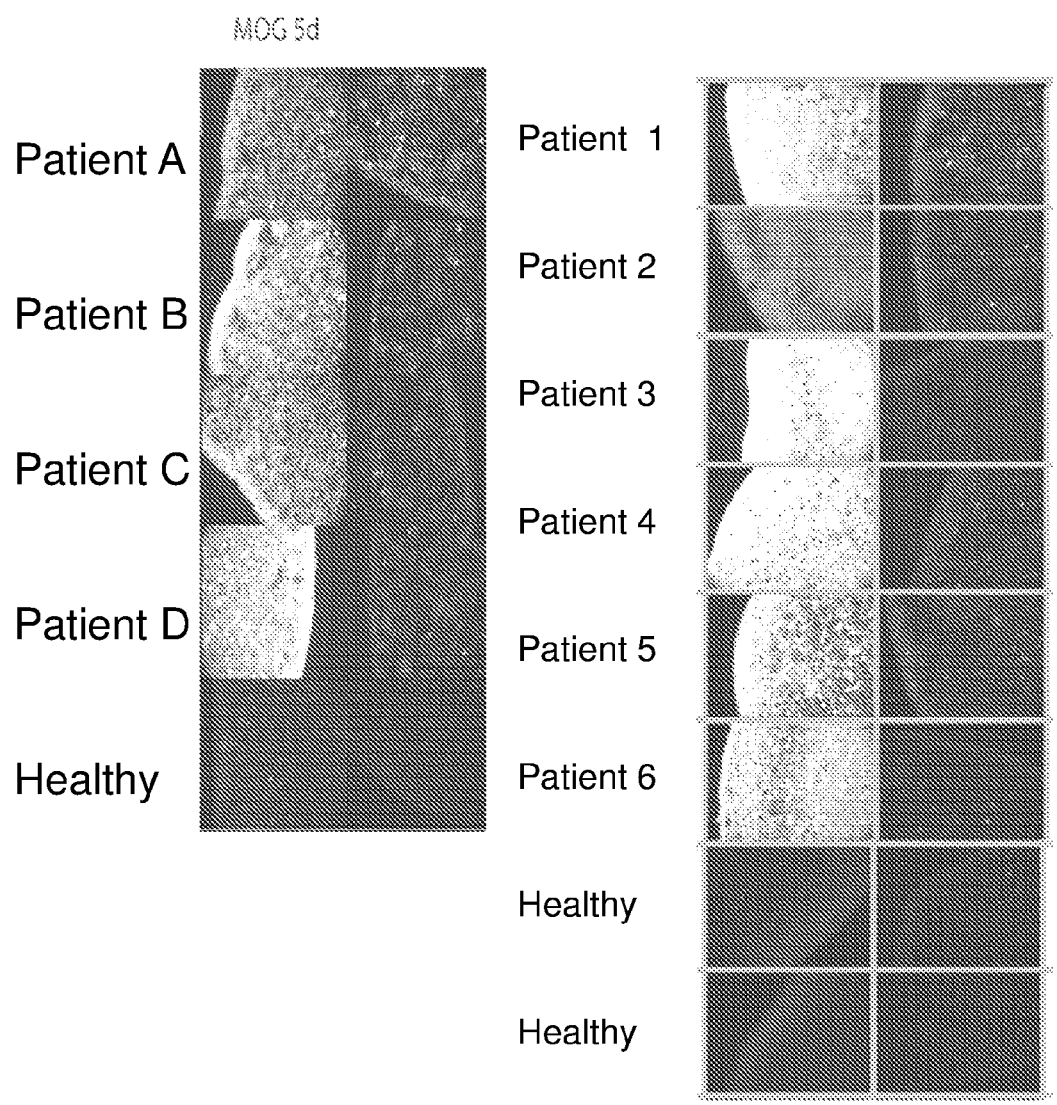
FIG. 6 shows that different types of antibodies can be detected using the vesicle approach of the invention. MOG antibodies are found in children and some adults with symptoms overlapping with neuromyelitis optica. Clinically it can be useful to measure AQP4 and MOG antibodies in parallel. CASPR2 antibodies are found in patients with different forms of encephalopathy and often also with peripheral nerve hyperexcitability. Patient sera with the relevant autoantibodies are shown binding to vesicles expressing either of these two antigens, comparing with healthy sera; each serum is tested against a control-transfected vesicle preparation. Patient 2 had only marginal positivity on the cell-based assay.

A test system has been produced that represents the native antigen(s) but does not require live cells. For this membrane vesicles have been prepared from the transfected antigen-expressing cells using standard methods. The proteins expressed by these membrane vesicles can be seen on the surface by freeze etching (FIG. 1). The antigens can be identified in the membrane preparations by western blotting. When the preparation of membrane vesicles are spotted onto PLL coated slides and allowed to air-dry, antibodies can be detected which bind to these dried antigen preparations (FIG. 2 right hand panels). As compared to typical cell-based assays, the membrane vesicle assay of the invention is highly specific and sensitive (FIGS. 3 and 4). In addition to being stable over time when stored in a dried form (FIG. 2), the preparation of membrane vesicles may also be stable over time when stored in any suitable buffer (FIG. 5). In addition to AQP4, the membrane vesicle assay of the invention has been show to detect MOG and CASPR2 autoantibodies. Diseases now recognised as associated with pathogenic autoantibodies are shown in Table 2 below.

TABLE 2

Examples of diseases and some of the autoantibodies now known to be clinically relevant to diagnosis and treatment

| Disease type | Clinical features | Antibodies known to be associated with the disease | Current methods for identification |
|---|---|---|---|
| Peripheral neurological diseases | | | |
| Myasthenia gravis, Lambert Eaton myasthenic syndrome | Muscle weakness, fatigue Neonatal myasthenia Arthrogryposis in baby of mother with myasthenia | Acetylcholine receptor (AChR), foetal AChR, muscle specific kinase (MuSK) voltage-gated calcium channel (VGCC) | Radioimmunoprecipitation for AChR, MuSK, VGCC, VGKC-complex. ELISA for AChR |
| Acquired neuromyotonia | Muscle twitching, cramps. Sensory symptoms and pain | Voltage-gated potassium channel-complex (VGKC-complex) proteins e.g. CASPR2, LGI1, Contactin-2 | Cell-based assays for CASPR2, LGI1, Contactin-2 and others to be identified |
| Brain and spinal cord diseases | | | |
| | Memory loss, seizures, psychological disturbance | VGKC-complex including LGI1, CASPR2, Contactin-2, glutamic acid decarboxylase (GAD) AMPA and GABAb receptors, mGluR5 receptor | Radioimmunoprecipitation for VGKC-complex and GAD antibodies. Cell-based antibodies for LGI1 CASPR2 AMPAR, GABABR, NMDAR, Glycine receptor and GAD |
| NMDAR-antibody encephalitis | Memory loss, seizures, psychological disturbance with additional movement disorders, autonomic disturbance and reduced consciousness | NMDAR (NR1 or NR1/NR2b) | Cell-based assay for NMDAR (NR1 or NR1/NR2b) |
| Cerebellar ataxia | Incoordination, lack of balance, dysarthria, dysphagia | VGKC-complex, CASPR2, glutamic acid decarboxylase (GAD), GluD2 | Cell-based antibodies for CASPR2 and GAD |
| Stiff person syndrome and progressive encephalomyelitis with rigidity and myoclonus | Loss of spinal and brain stem inhibition causing stiffness, rigidity, spasms, autonomic disturbance | Glycine receptor, GAD | Radioimmunoprecipitaton assays for GAD No commercial assay for glycine receptor |
| Demyelinating inflammatory disorders: Neuromyelitis optica and acute dessiminated encephalomyelitis (ADEM) | Optic neuritis leading to reduced vision or blindness; transverse myelitis leading to pain, sensory symptoms, paralysis As above but with more brain involvement, leading to a variety of symptoms | Aquaporin-4 (AQP4) and myelin-oligodendrocyte glycoprotein (MOG) | ELISA for AQP4; cell-based assay for AQP4 and MOG |

The invention claimed is:

1. A method of measuring from a sample from an individual the presence or absence of one or more autoantibodies each directed against an antigen, the method comprising:
    transforming or transfecting a cell with polynucleotide sequences that encode the one or more antigens,
    expressing said one or more antigens in the cell;
    collecting membrane vesicles from said cell to obtain a preparation of membrane vesicles comprising said one or more antigens;
    drying said membrane vesicles;
    contacting the sample from the individual with said preparation of membrane vesicles comprising the one or more antigens; and
    measuring for the presence or absence of the one or more autoantibodies by detecting in the sample from the individual whether or not one or more autoantibodies in the sample binds to said one or more antigens,
    wherein said one or more antigens are selected from the group consisting of aquaporin-4 (AQP4), myelin-oligodendrocyte glycoprotein (MOG), acetylcholine receptor, muscle specific tyrosine kinase (MuSK), N-methyl-D-aspartate (NMDA) receptor, leucine-rich glioma inactivated protein 1 (LGI1), contactin associated protein-like 2 (CASPR2), glycine receptor alpha 1, gamma-aminobutyric acid type B (GABA-B) receptor and a combination thereof.

2. A method according to claim 1, wherein the membrane vesicles are exosomes.

3. A method according to claim 1, wherein the membrane vesicles are:
   (a) substantially isolated from cells;
   (b) isolated from cells; or
   (c) present in a ratio of more than 5,000 membrane vesicles per cell.

4. A method according to claim 1, wherein the membrane vesicles are:
   (a) dried;
   (b) attached to a solid support; or
   (c) derived from a cell transfected or transformed with the antigen.

5. A method according to claim 1, wherein the presence or absence of the one or more autoantibodies are detected by an enzyme-linked immunosorbent assay (ELISA), radioimmunoassay, competition assay, inhibition assay, sandwich assay, fluorescent microscopy, microarray or fluorescence-activated cell sorting (FACS) analysis.

6. A method according to claim 1, wherein when the presence of the one or more autoantibodies in the individual is identified, the individual is administered a therapeutically effective amount of an immunotherapy.

7. The method of claim 1, wherein the individual is a mother having an unborn baby and when the presence of the one or more autoantibodies in the mother is identified, the mother is administered a therapeutically effective amount of an immunotherapy.

8. The method of claim 1, wherein said antigen is acetylcholine receptor and said membrane vesicles comprising the acetylcholine receptor co-express rapsyn.

9. The method of claim 1, wherein said antigen is NMDA receptor and said membrane vesicles comprising NMDA receptor co-express postsynaptic density protein (PSD).

* * * * *